(12) United States Patent
Fukuda

(10) Patent No.: US 8,627,722 B2
(45) Date of Patent: Jan. 14, 2014

(54) WELDING INSPECTION METHOD AND WELDING INSPECTION APPARATUS

(75) Inventor: Hiroshi Fukuda, Tokyo (JP)

(73) Assignee: Hino Motors, Ltd. (JP)

( * ) Notice: Subject to any disclaimer, the term of this patent is extended or adjusted under 35 U.S.C. 154(b) by 232 days.

(21) Appl. No.: 12/865,570

(22) PCT Filed: Jan. 19, 2009

(86) PCT No.: PCT/JP2009/000160
§ 371 (c)(1), (2), (4) Date: Jul. 30, 2010

(87) PCT Pub. No.: WO2009/096146
PCT Pub. Date: Aug. 6, 2009

(65) Prior Publication Data
US 2010/0326196 A1    Dec. 30, 2010

(30) Foreign Application Priority Data

Jan. 30, 2008   (JP) ................. 2008-019543

(51) Int. Cl.
*G01N 29/04*   (2006.01)

(52) U.S. Cl.
USPC ......................... 73/588; 73/626; 73/641

(58) Field of Classification Search
USPC ................... 73/588, 626, 641, 644
See application file for complete search history.

(56) References Cited

U.S. PATENT DOCUMENTS

| | | | | |
|---|---|---|---|---|
| 4,375,165 A | * | 3/1983 | de Sterke | 73/622 |
| 6,072,144 A | * | 6/2000 | Perryman | 219/109 |
| 6,414,260 B1 | * | 7/2002 | Vogt | 219/109 |
| 6,948,369 B2 | * | 9/2005 | Fleming et al. | 73/588 |
| 7,577,533 B2 | * | 8/2009 | Buschke et al. | 702/39 |
| 7,698,944 B2 | * | 4/2010 | Takada | 73/588 |
| 7,779,694 B2 | * | 8/2010 | Iizuka | 73/622 |
| 7,798,002 B2 | * | 9/2010 | Tanishiki | 73/620 |
| 2005/0224562 A1 | * | 10/2005 | Prevey | 228/233.1 |
| 2007/0240512 A1 | * | 10/2007 | Takada | 73/588 |

FOREIGN PATENT DOCUMENTS

| | | |
|---|---|---|
| JP | 59-193350 A | 11/1984 |
| JP | 62-222160 A | 9/1987 |
| JP | 63-163271 A | 7/1988 |
| JP | 02-064451 A | 3/1990 |

(Continued)

OTHER PUBLICATIONS

International Search Report for International Application No. PCT/JP2009/000160 mailed Apr. 28, 2009 with English translation.

(Continued)

*Primary Examiner* — J M Saint Surin
(74) *Attorney, Agent, or Firm* — Cantor Colburn LLP

(57) ABSTRACT

Disclosed is a welding inspection method which does not require the inspector to be highly skilled, does not require waiting for the spot welded part to cool off, and with which the probe is not consumed or damaged. A probe temporarily mounted close to the welded part on the surface of a metal plate emits ultrasonic waves from an oblique direction with respect to the boundary surfaces between a plurality of metal plates. At this time, the probe is temporarily mounted at the position where the incident ultrasonic waves pass through the welded part at the boundary between the plurality of metal plates in an oblique direction with respect to the boundary surface. Also, a display processing means displays the intensity of the refracted ultrasonic waves. Alternatively, the display processing means displays the details of the detection result estimated based on the intensity of the reflected ultrasonic waves.

10 Claims, 16 Drawing Sheets

(56) References Cited

FOREIGN PATENT DOCUMENTS

| JP | 5-322857 A | 12/1993 |
| JP | 11-118771 A | 4/1999 |
| JP | 3564683 B2 | 6/2004 |
| JP | 2006-071422 A | 3/2006 |
| JP | 2006-153710 A | 6/2006 |
| JP | 2007-232525 | 9/2007 |
| JP | 2007-232526 A | 9/2007 |
| WO | 86/04416 | 7/1986 |

OTHER PUBLICATIONS

Office Action for Japanese Patent Application No. 2008-019543, mailed Apr. 2, 2013, with English translation.

* cited by examiner

WELDING INSPECTION METHOD AND WELDING INSPECTION APPARATUS

CROSS REFERENCE TO RELATED APPLICATIONS

This is a U.S. national stage application of International Application No. PCT/JP/2009/000160, filed on 19 Jan. 2009. Priority under 35 U.S.C. §119(a) and 35 U.S.C. §365(b) is claimed from Japanese Application No. 2008-019543, filed 30 Jan. 2008, the disclosure of which is also incorporated herein by reference.

BACKGROUND OF THE INVENTION

1. Field of the Invention

The present invention relates to a method and an apparatus of welding inspection.

2. Description of Related Art

Welding is in heavy usage for assembly processes of automobiles. A reason for the heavy usage of welding is that structural members made by matching edges of thin steel plates and welding the matched edges are used in quite a few cases in such assembly processes. For example, a frame of a truck is made by bending a thick steel plate into a horseshoe shape. Used for a cabin and a roof in this case are structural members with their cross sections of a square pipe made of a combination of bent thin steel plates. As described above, structural members made of thin steel plates press-bent and welded are used in a great number in manufacturing processes of automobiles.

An inspection method using ultrasonic waves is described below with reference to FIG. 1 through FIG. 9, as a conventional welding inspection method in relation to the present invention. FIGS. 1 and 2 are drawings that explain the conventional welding inspection method, and show a positional relationship between a conventional ultrasonic probe 10 (hereinafter, simply called a "probe") and a combination of steel plates 13-1 and 13-2 as specimens. FIG. 3 is a drawing for showing a welded part 12 (hereinafter, called a "nugget"). Though spot welding is described in the following explanation, a scope of application of the present invention is not limited to the spot welding.

The probe 10 includes a transducer 11, which is equipped with a sending/receiving element for ultrasonic waves. The transducer 11 is connected to a welding inspection apparatus, which is not shown in the drawing; and the transducer 11 sends and receives an ultrasonic wave as a pulse signal. The welding inspection apparatus receives a reflected ultrasonic wave at each time of sending a pulse signal in order to measure the intensity of the reflected ultrasonic wave.

Furthermore, the probe 10 includes a contacting part 14, which is internally charged with a liquid such as water. Thus, an ultrasonic wave launched from the transducer 11 can efficiently be transmitted to the steel plate 13-1. The contacting part 14 is formed with an elastic material such as rubber so that the condition of contact between the probe 10 and the steel plate 13-1 does not change even when a posture tilt of the probe 10 changes somewhat.

As shown in FIG. 3, the nugget 12 is formed at a boundary plane between the plurality of steel plates 13-1 and 13-2 being stacked. In an example of FIG. 3, the two steel plates 13-1 and 13-2 are stacked. However, the number of stacked steel plates may be more than two under the same structural concept.

As shown in FIGS. 1 and 2, in the conventional welding inspection method using an ultrasonic wave, the probe 10 needs to be placed right above the nugget 12, namely to be placed right on a spot-welded section 15.

A reason for such an arrangement described above is that, for materialization of the inspection, an ultrasonic wave launched from the probe 10 must indispensably pass through the nugget 12, meanwhile the probe 10 must receive a reflected wave of the ultrasonic wave. Therefore, the probe 10 is necessarily placed right on the spot-welded section 15. Furthermore, to efficiently receive the reflected ultrasonic wave, a reflection plane for the ultrasonic wave needs to be almost perpendicular to a traveling direction of the ultrasonic wave, and accordingly the probe 10 requires an adequate accuracy on a tilt adjustment.

FIGS. 4 to 9 are drawings for explaining a concrete example of the conventional welding inspection method using an ultrasonic wave. FIG. 5 shows a graph of an inspection result of the nugget 12 that is made up normally; and in the graph, a horizontal axis and a vertical axis are a time axis and axis of an intensity of the reflected ultrasonic wave, respectively.

The ultrasonic wave launched toward the steel plate 13-1 from the probe 10 travels back and forth several times between a top surface of the steel plate 13-1 and a bottom surface of the steel plate 13-2 in a certain time period, and eventually an energy of the ultrasonic wave is attenuated to disappear. While the ultrasonic wave travels back and forth within the steel plates 13-1 and 13-2, a part of the ultrasonic wave reflected between the top surface of the steel plate 13-1 and the bottom surface of the steel plate 13-2 returns to the probe 10. An example of a waveform image of the ultrasonic wave for enabling an inspector to visually check it by using an image display apparatus (an oscilloscope) is shown in FIG. 5, the ultrasonic wave having returned to the probe 10.

FIG. 5 shows a waveform of an ultrasonic wave in the case where the nugget 12 is made up normally. In this case, several repetitive waveform peaks according to thicknesses of the steel plates 13-1 and 13-2 appear; and the repetitive waveform peaks result in a certain attenuation curve, and such a waveform pattern is output. A quality judgment on the nugget 12 is carried out through evaluation of the number of waveform peaks, a level of each waveform peak, a distance between two neighboring waveform peaks, presence of any waveform peak that should not appear primarily, and others.

A speed of the ultrasonic wave traveling in the nugget 12 is constant. Therefore, a plurality of reflected ultrasonic waves, which are reflected at the bottom surface of the steel plate 13-2, appear at intervals of transmission time of the ultrasonic waves, corresponding to the thicknesses of the steel plates 13-1 and 13-2. Accordingly, the horizontal axis in FIG. 5 is a time axis that represents a distance in a thickness direction of the steel plates 13-1 and 13-2 (for example, refer to Patent Document 1).

On the contrary, FIG. 6 shows another case in which the nugget 12 is not made up normally, having a gap or pealed between the steel plates 13-1 and 13-2. FIG. 7 shows a graph of an inspection result of the nugget 12 that is a defective one having the pealed; and in the graph, a horizontal axis and a vertical axis are a time axis and axis of an intensity of the reflected ultrasonic wave, respectively.

Under a condition where the nugget 12 is not made up normally, having a pealed between the steel plates 13-1 and 13-2, as shown in FIG. 7, there appear repetitive waveforms with a less attenuation due to the plate thickness at a searching surface side. Namely, if there exists a pealed between the steel plates 13-1 and 13-2, an ultrasonic wave launched from the probe 10 travels back and forth only between the top surface and a bottom surface of the steel plate 13-1. Accordingly, in comparison with the example shown in FIG. 5, a traveling distance of the ultrasonic wave is shorter so that peak intervals become shorter than those shown in FIG. 5. Furthermore, the short traveling distance of the ultrasonic wave results in a less attenuation in comparison with the example shown in FIG. 5 so that peaks having the same intensity consecutively appear at short intervals. When such peaks appear, it is determined that there exists a pealed between the steel plates 13-1 and 13-2.

FIG. 8 shows still another case in which the nugget 12 is made to be small. FIG. 9 shows a graph of an inspection result of the nugget 12 that is made to be small; and in the graph, a horizontal axis and a vertical axis are a time axis and axis of an intensity of the reflected ultrasonic wave, respectively.

Under a condition where the nugget 12 is made smaller than in a normal case, there appears a condition equivalent to including two modes in parallel within an inspection area of the probe 10; namely, one mode with the nugget 12 made up normally as shown in FIG. 5 and the other mode having the pealed shown in FIG. 7. Accordingly, in a waveform there appear together the large peaks shown in FIG. 5 as well as the small peaks shown in FIG. 7. The small peaks existing between the large peaks are distinctively called "Napoleon hats". When such Napoleon hats appear, it can be determined that the nugget 12 is made smaller than in a normal case.

As described above, in the conventional welding inspection method, the probe 10 for executing the inspection is placed right above the nugget 12 to be almost perpendicular to the steel plate 13-1.

LIST OF BACKGROUND ART DOCUMENT

Patent Document 1: JP 2006-153710 A
Patent Document 2: JP 2006-71422 A
Patent Document 3: JP 2007-232525 A
Patent Document 4: JP 2007-232526 A

SUMMARY OF THE INVENTION

In the conventional welding inspection method, the probe needs to be placed right above the nugget, namely to be placed right on the spot-welded section, being perpendicular to the steel plate for accurate measurement. If an inspector carries out the placement and alignment manually, it is hardly possible to eliminate uncertainty about the inspection accuracy depending on a skill level of the inspector.

Furthermore, before placing the probe onto the spot-welded section, the inspector must wait for the spot-welded section to be cooled down. Accordingly, inspection work efficiency may is decreased.

Moreover, usually the probe is equipped with a contacting part (the reference numeral 14 in FIG. 1) formed with an elastic material such as rubber. Pressing the contacting part against a steel plate materializes a condition of full contact between the probe and the steel plate. However, when the contacting part formed with such a soft material is put into the condition of full contact with the spot-welded section for inspection work, the contacting part may be worn out and/or damaged easily.

Thus, it is an object of the present invention to solve the subjects described above; namely to provide a welding inspection method and a welding inspection apparatus which do neither need the inspector to have a sufficient level of skill, nor need to wait for the spot-welded section to be cooled down to low temperature, and in which the contacting part is not worn out and/or damaged easily.

MEANS TO SOLVE THE SUBJECTS

In the view of the present invention as a welding inspection method, the welding inspection method for quality check on a welding carried out for a plurality of stacked metal plates includes: launching an ultrasonic wave to a boundary plane of the plurality of metal plates from an oblique direction through a probe temporarily placed in the proximity of a welded part on a surface of the metal plates.

On this occasion, the probe may be temporarily placed at such a position that an ultrasonic wave having entered the boundary plane of the metal plates from an oblique direction passes through the nugget created in the boundary plane of the plurality of metal plates.

Furthermore, display processing means may display an image of a reflected wave of the ultrasonic wave. Otherwise, display processing means may display the contents of an inspection result estimated according to an intensity of the reflected wave of the ultrasonic wave. Alternatively, display processing means may output information showing the inspection result estimated according to the intensity of the reflected wave of the ultrasonic wave, to an external device.

For example, the welding may be carried out as a spot welding.

According to the welding inspection method, it is not necessary to place the probe right above the nugget, namely right on the spot-welded section, to be almost perpendicular to the steel plates; and therefore the welding inspection can be carried out accurately, being irrelevant to the skill level of the inspector.

Furthermore, since placing the probe right on the spot-welded section is not needed, it is not necessary to wait for the spot-welded section to be cooled down so that the inspection work efficiency can be improved.

Moreover, the probe does not have a contacting part formed with an elastic material such as rubber, and therefore the probe is not worn out and/or damaged easily.

In the view of the present invention as a welding inspection apparatus, the welding inspection apparatus for quality check on a welding carried out for a plurality of stacked metal plates includes: a probe to be temporarily placed in the proximity of a welded part on a surface of the metal plates; and means for launching an ultrasonic wave to a boundary plane of the plurality of metal plates from an oblique direction through the probe.

The welding inspection apparatus may further include display processing means for displaying an image of a reflected wave of the ultrasonic wave. Otherwise, the welding inspection apparatus may further include display processing means for displaying the contents of an inspection result estimated according to an intensity of the reflected wave of the ultrasonic wave. Alternatively, the welding inspection apparatus may further include display processing means for outputting information showing the inspection result estimated according to the intensity of the reflected wave of the ultrasonic wave, to an external device.

According to the present invention, the welding inspection can be carried out accurately, being irrelevant to the skill level of the inspector. Furthermore, the probe is not worn out and/or damaged easily. Moreover, the inspection result does not depend on the accuracy of the form of the welded section. As a result, the inspection work efficiency can be improved.

BRIEF DESCRIPTION OF THE DRAWINGS

Specific embodiments of the present invention will now be described, by way of example only, with reference to the accompanying drawings in which.

DETAILED DESCRIPTION OF THE PREFERRED EMBODIMENTS

Figure 10:
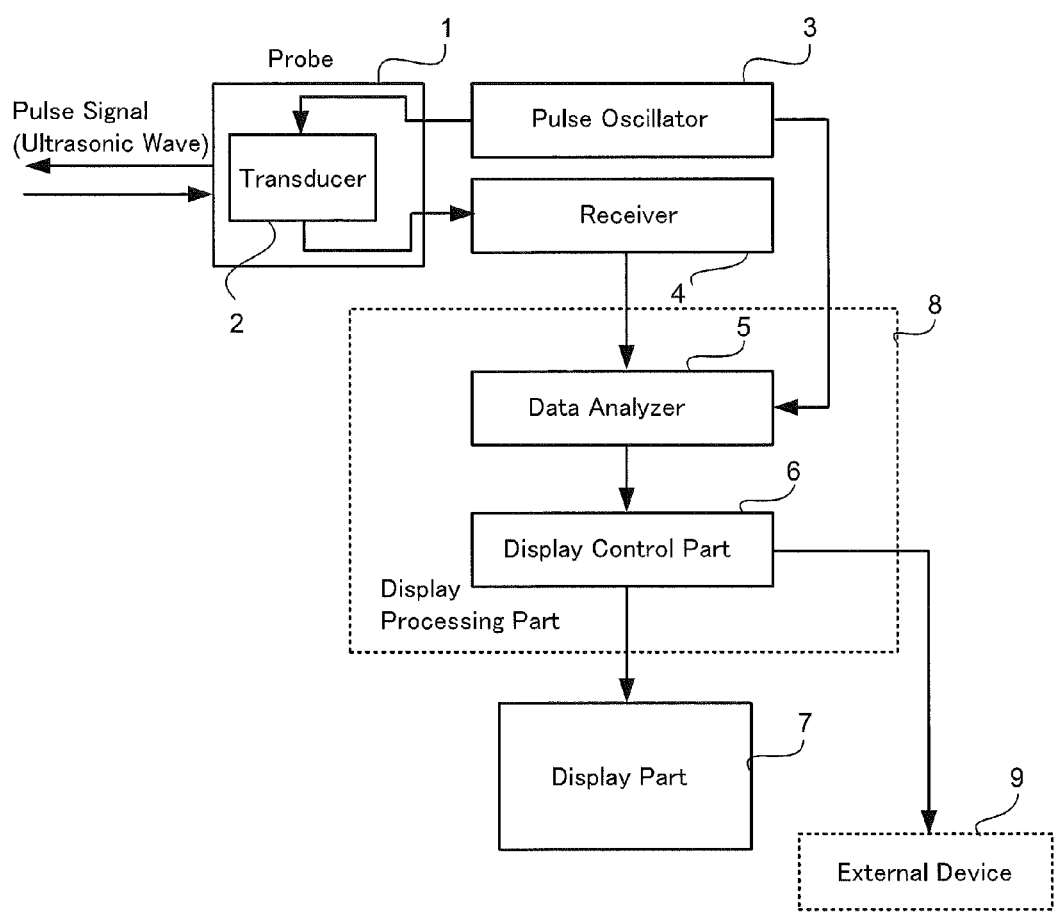
FIG. 10 is a block diagram of a welding inspection apparatus according to an embodiment of the present invention.

An embodiment of the present invention is described below with reference to FIG. 10 through FIG. 23. FIG. 10 is a block diagram of a welding inspection apparatus according to an embodiment of the present invention. As shown in FIG. 10, the welding inspection apparatus according to the embodiment of the present invention includes a probe 1 to be temporarily placed in the proximity of a welded section on a surface of a steel plate 13-1, and a transducer 2 as means for launching an ultrasonic wave to a boundary plane between steel plates 13-1 and 13-2 from an oblique direction through the probe 1.

Furthermore, the welding inspection apparatus includes a display processing part 8 as display processing means for displaying an image of a reflected wave of the ultrasonic wave. In another configuration, the display processing part 8 may be display processing means for displaying the contents of an inspection result estimated according to an intensity of the reflected wave of the ultrasonic wave. Moreover, the display processing part 8 can also output information such as "Normal", "Pealed Exist", "Small Nugget", etc., to an external device 9; which is, for example, one of a storage device, a transfer device, an error alarming device, and the like for inspection results.

In the following explanation, spot welding is described. However, a scope of application of the embodiment of the present invention is not limited to the spot welding.

The transducer 2 is equipped with a sending/receiving element for ultrasonic waves (not shown). A pulse oscillator 3 provides the sending/receiving element of the transducer 2 for an ultrasonic wave with a pulse signal as an electric signal. Being provided with the pulse signal as an electric signal, the sending/receiving element for an ultrasonic wave generates an ultrasonic wave in response to the provided pulse signal. Moreover, the sending/receiving element for an ultrasonic wave receives a pulse signal as a reflected wave of the ultrasonic wave, and converts it into an electric signal to output to a receiver 4. Thus, the receiver 4 converts the pulse signal as a reflected wave of the ultrasonic wave, launched from the sending/receiving element of the transducer 2 as an electric signal, into a signal format receivable for a data analyzer 5; and outputs the converted pulse signal to the data analyzer 5.

The data analyzer 5 receives pulse signals from the receiver 4 and the pulse oscillator 3, and then analyzes differences in time and intensity between the pulse signals received from both the two components. Through the analysis operation, it can be analyzed how an ultrasonic wave launched from the probe 1 is reflected and attenuated through the steel plates 13-1 and 13-2.

An analysis result from the data analyzer 5 is sent to the display control part 6, which shows the analysis result as an image of a waveform recognizable by an inspector, or as textual information indicating "Normal", "Pealed Exist", "Small Nugget", etc., in a display part 7. Otherwise, such information of "Normal", "Pealed Exist", "Small nugget", etc. is output to an external device 9. The external device 9 is, for example, one of a storage device, a transfer device, an error alarming device, and the like for inspection results.

Figure 11:
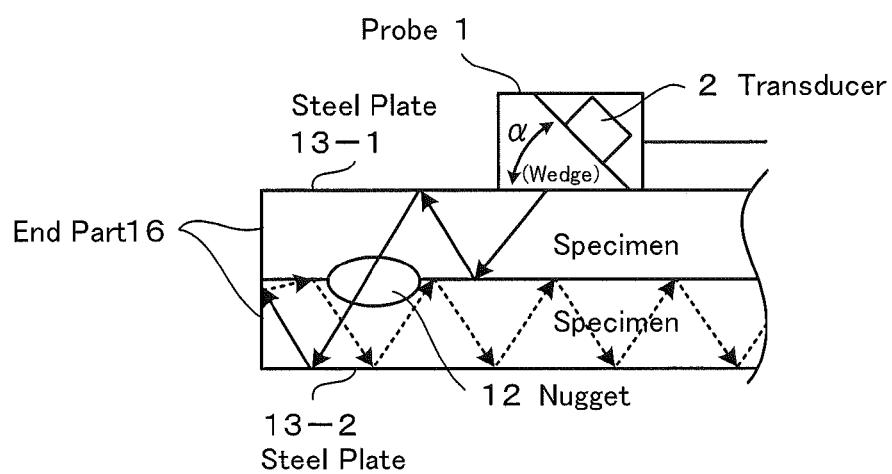
FIG. 11 is a drawing for explaining a welding inspection method according to an embodiment of the present invention.
Figure 12A:
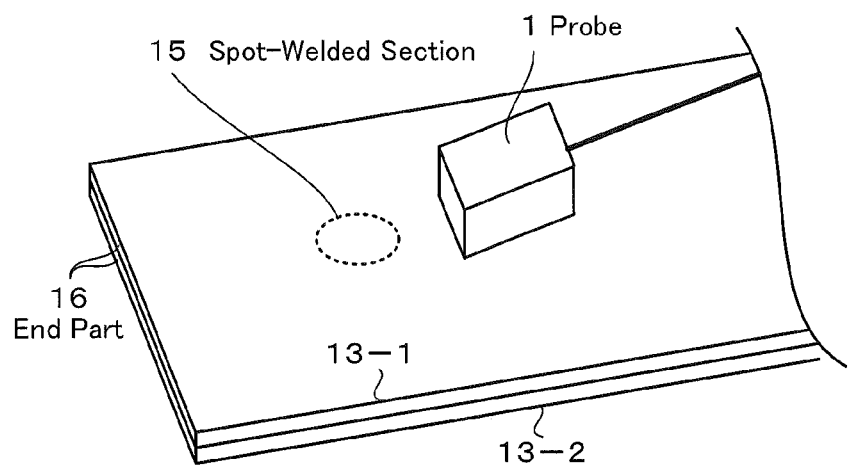
FIGS. 12A and 12B are drawings for explaining the welding inspection method according to the embodiment of the present invention.
Figure 12B:
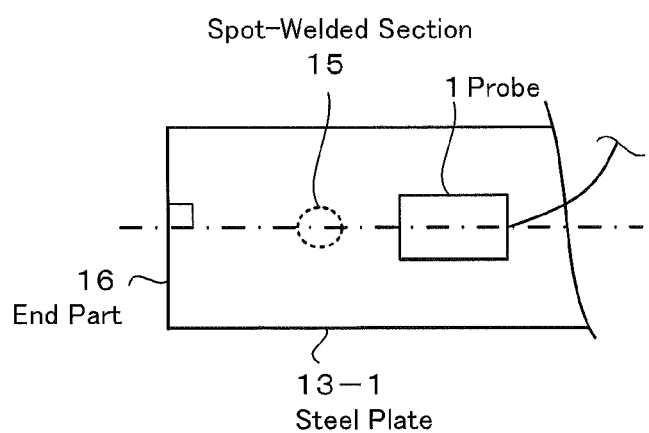

FIGS. 11, 12A and 12B are drawings for explaining the welding inspection method according to the embodiment of the present invention, and these drawings show a positional relationship between the probe 1 and the combination of steel plates 13-1 and 13-2 as specimens according to the embodiment of the present invention.

As shown in FIGS. 11, 12A and 12B, the welding inspection method using an ultrasonic wave according to the embodiment of the present invention does not need to have the probe 1 placed right above a nugget 12, namely does not need to have the probe 1 placed right on a spot-welded section 15. In other words, inspection can be carried out while the probe 1 being temporarily placed in the proximity of the spot-welded section 15 on a surface of the steel plate 13-1.

More specifically, as shown in FIG. 11, an ultrasonic wave launched from the transducer 2 enters the steel plate 13-1 through the probe 1. At a boundary plane where the steel plates 13-1 and 13-2 are not combined, the ultrasonic wave having entered the steel plate 13-1 does not enter a side of the steel plate 13-2; whereas the ultrasonic wave passes through the nugget 12 where the steel plates 13-1 and 13-2 are combined, and enters the steel plate 13-2. The ultrasonic wave having entered the steel plate 13-2 is reflected at an end part 16 of the steel plate 13-2 to return inside the steel plate 13-2.

Thus, the welding inspection method using an ultrasonic wave according to the embodiment of the present invention makes it possible to recognize conditions of the nugget 12 by detecting the ultrasonic wave reflected at the end part 16 of the steel plates 13-1 and 13-2. Therefore, as shown in FIGS. 12A and 12B, indispensably the probe 1 is so placed temporarily on the steel plate 13-1 that the nugget 12 (or, the spot-welded section 15) exists between the end part 16 and the probe 1. Furthermore, the probe 1 is so oriented in a direction to launch an ultrasonic wave toward the nugget 12 (or, the spot-welded section 15).

Moreover, as shown in FIG. 12B, the ultrasonic wave is launched from the probe 1 in a direction (as shown with a dashed line in the figure) perpendicular to a surface of the end part 16. Then, the ultrasonic wave launched from the probe 1 is so reflected at the end part 16 that the reflected ultrasonic wave efficiently returns in a direction toward the probe 1, and accordingly the inspection can be carried out with high accuracy.

Figure 1:
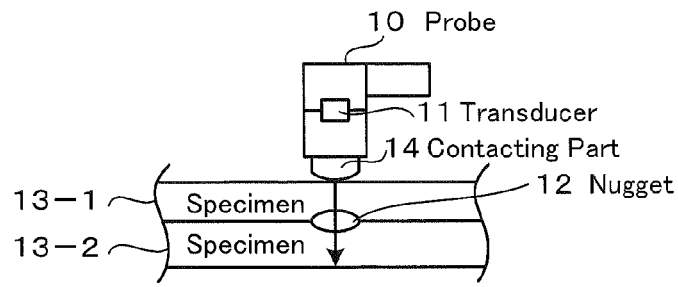
FIG. 1 is a drawing that explains a conventional welding inspection method.
Figure 2:
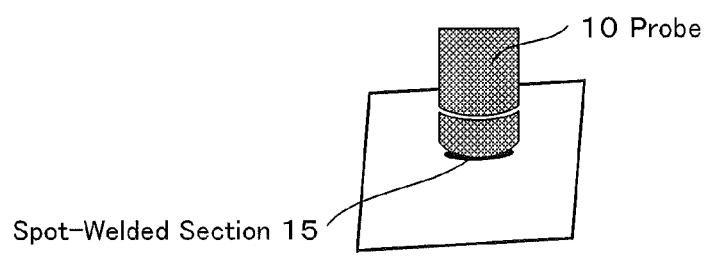
FIG. 2 is a drawing that explains a conventional welding inspection method.
Figure 3:
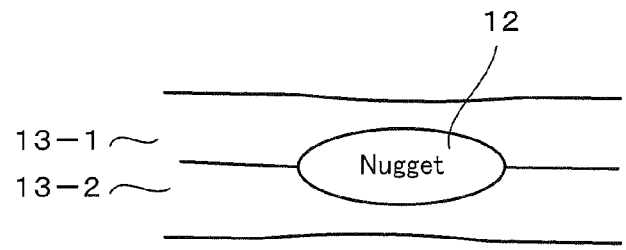
FIG. 3 is a drawing for showing a nugget.
Figure 4:
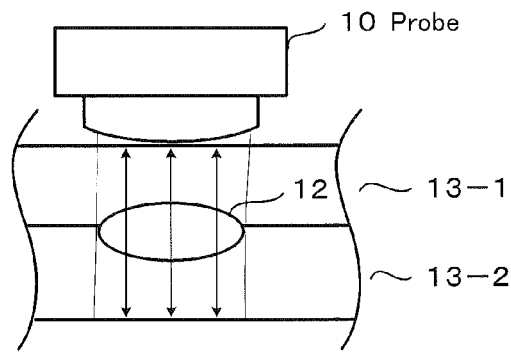
FIG. 4 is a drawing for explaining a concrete example of the conventional welding inspection method using an ultrasonic wave (in the case where the nugget is made up normally)
Figure 5:
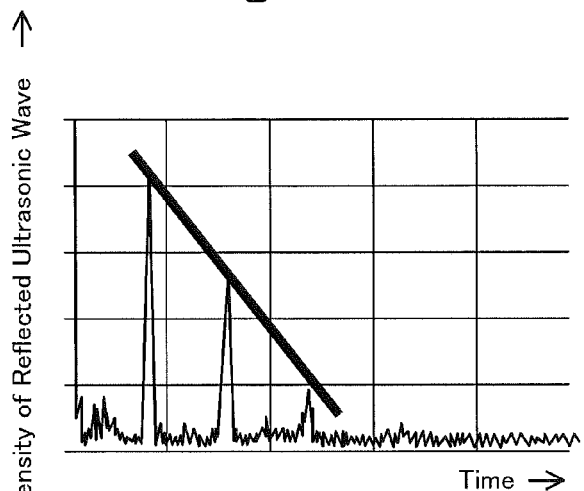
FIG. 5 shows a graph of an inspection result of the conventional welding inspection method on the nugget made up normally.
Figure 6:
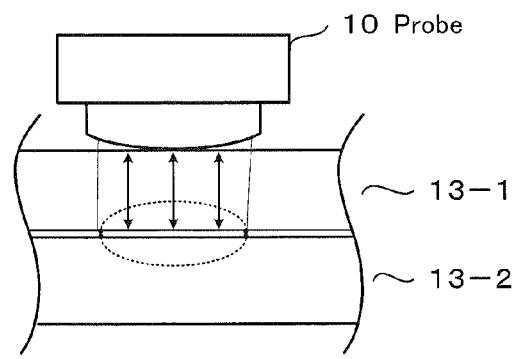
FIG. 6 is a drawing for explaining a concrete example of the conventional welding inspection method using an ultrasonic wave (in the case where the nugget is not made up normally, having a pealed between the steel plates)
Figure 7:
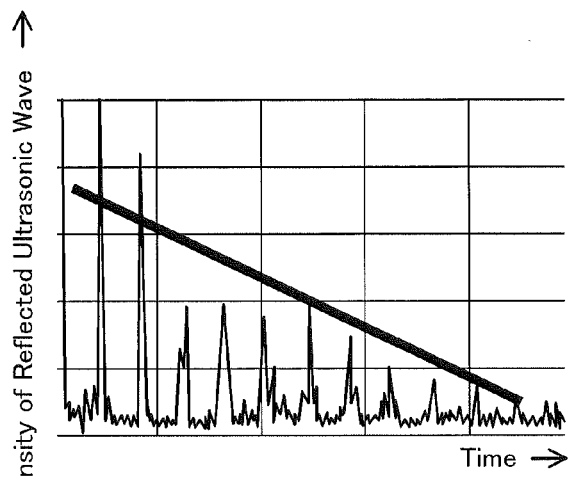
FIG. 7 shows a graph of an inspection result of the conventional welding inspection method on the defective nugget having the pealed between the steel plates.
Figure 8:
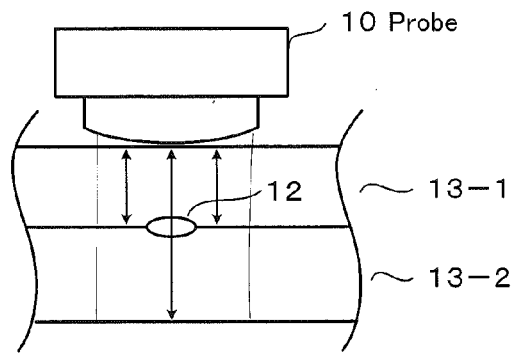
FIG. 8 is a drawing for explaining a concrete example of the conventional welding inspection method using an ultrasonic wave (in the case where the nugget is made to be small)
Figure 9:
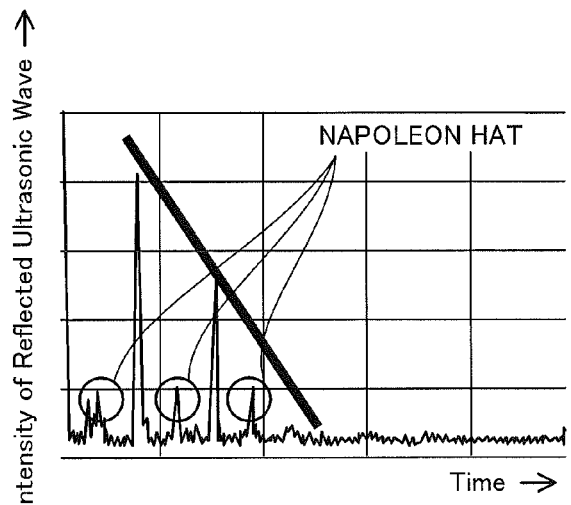
FIG. 9 shows a graph of an inspection result of the conventional welding inspection method on the small nugget.

On the other hand, in an example of a conventional way as shown in FIGS. 1 and 2, for placing the probe 10 right above the nugget 12 (or, right on the spot-welded section 15) to be perpendicular to the steel plate 13-1 through the inspection, an inspector needs to keep on holding the probe 10 by hand to make it being perpendicular to the steel plate 13-1 all through the inspection. At this time, it is judged only through uncertain visual check by the inspector whether the probe 10 is held to be perpendicular to the steel plate 13-1 or not. Eventually, the inspector needs to have an enough level of skill.

In the meantime, according to the embodiment of the present invention, the probe 1 is so placed temporarily on the steel plate 13-1 that the ultrasonic wave is launched from the probe 1 in the direction perpendicular to the surface of the end part 16, as shown in FIG. 12B. At this time of placing the probe 1 temporarily, the inspector can easily check the orientation of the probe 1 with respect to the surface of the end part 16 by observing a maximum intensity of the reflected ultrasonic wave while swinging the probe 1. Thus, an optimum posture of placing the probe 1 temporarily can be adjusted easily, and the inspector does not need to have a certain level of skill. Moreover, a workability of the inspection is improved in comparison with that of the example of the conventional welding inspection method.

Furthermore, making an adjustment for an angle "α" formed by the transducer 2 and the steel plate 13-1 shown in FIG. 11 enables an adjustment for an optimum angle of the transducer 2 with respect to thicknesses of the steel plates 13-1 and 13-2. Namely, through the adjustment for an angle "α", an adjustment can be made for an incident angle of the ultrasonic wave launched from the probe 1 with respect to the surface of the steel plate 13-1. Therefore, the inspection is applicable for the steel plates 13-1 and 13-2 having various thicknesses.

Furthermore, it is preferable that the size of the probe 1 is almost equal to or smaller than the diameter of the nugget 12 as an inspection object. This is because, for example, the size of the probe 1 larger than the diameter of the nugget 12 results in an entrance of the ultrasonic wave outside the nugget 12 so that reflected ultrasonic waves unnecessary for the inspection (noise) are generated.

Thus, the welding inspection method according to the embodiment of the present invention can solve the problems that the conventional welding inspection method has. Namely, it is not necessary to place the probe 1 right on the spot-welded section 15 to be perpendicular to the steel plate 13-1, as described above. Then, the welding inspection can be carried out with high accuracy, being irrelevant to the skill level of the inspector.

Furthermore, placing the probe 1 right on the spot-welded section 15 is not needed. Accordingly, it is not necessary to wait for the spot-welded section 15 to be cooled down, and this enables avoidance of the problem that the inspection work efficiency is decreased.

A wedge part, at which the probe 1 and the steel plate 13-1 directly contact each other, can be made of a hard substance such as an acrylic material. Therefore, the wedge part is not as worn out and/or damaged as the contacting part 14 of the example of the conventional welding inspection method is.

Figure 13:
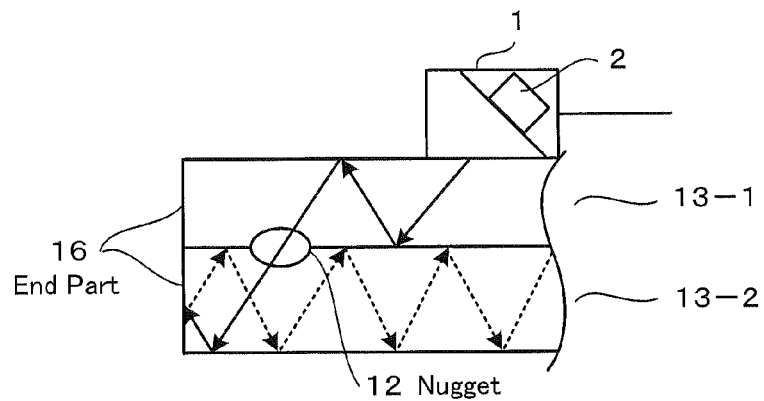
FIG. 13 is a drawing for explaining a concrete example of the welding inspection method using an ultrasonic wave according to the embodiment of the present invention (in the case where the nugget is made up normally)
Figure 14:
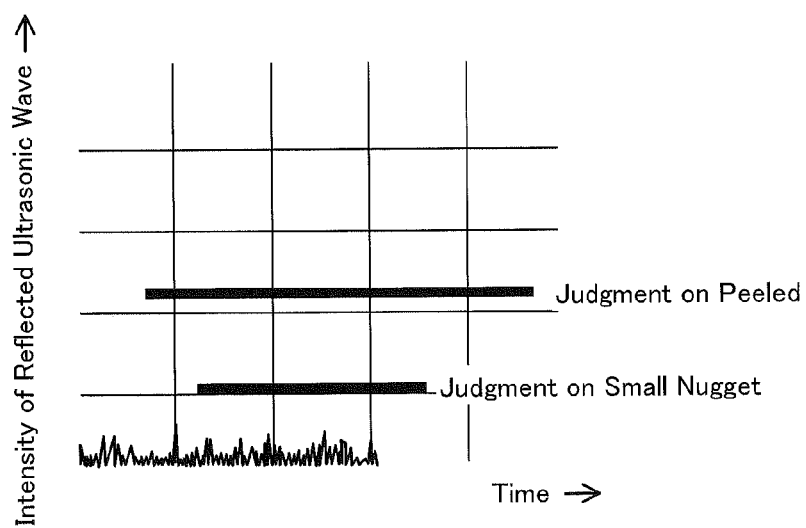
FIG. 14 shows a graph of an inspection result of the welding inspection method according to the embodiment of the present invention on the nugget made up normally.

FIGS. 13 to 18 are drawings for explaining a concrete example of the welding inspection method using an ultrasonic wave according to the embodiment of the present invention. FIG. 13 is a figure showing a case where the nugget 12 is made up normally. FIG. 14 shows a graph of an inspection result on the nugget 12 made up normally; and in the graph, a horizontal axis and a vertical axis are a time axis and axis of an intensity of the reflected ultrasonic wave, respectively.

As shown in FIG. 13, the probe 1 is temporarily placed at an appropriate position, as described above, in the proximity of the spot-welded section 15. Then, the ultrasonic wave having entered the steel plate 13-1 passes through the nugget 12 to enter the steel plate 13-2. Thus, the ultrasonic wave having entered the steel plate 13-2 is reflected at the end part 16 of the steel plate 13-2, then repeatedly reflected inside the steel plate 13-2, and the ultrasonic wave scarcely does return to the steel plate 13-1. Accordingly, there appears almost no reflected ultrasonic wave, as FIG. 14 shows.

Therefore, at first in the inspection work procedures, the probe 1 is so placed temporarily on the steel plate 13-1 that the ultrasonic wave is launched from the probe 1 in the direction perpendicular to the surface of the end part 16, and the spot-welded section 15 exists between the end part 16 and the probe 1. Then, a posture of the probe 1, which gives a prescribed minimum value of the reflected ultrasonic wave, is searched for while the probe 1 is shifted little by little.

When the posture for giving the prescribed minimum value of the reflected ultrasonic wave cannot be found, it is judged that the objective part has not been welded appropriately, as described below.

Figure 15:
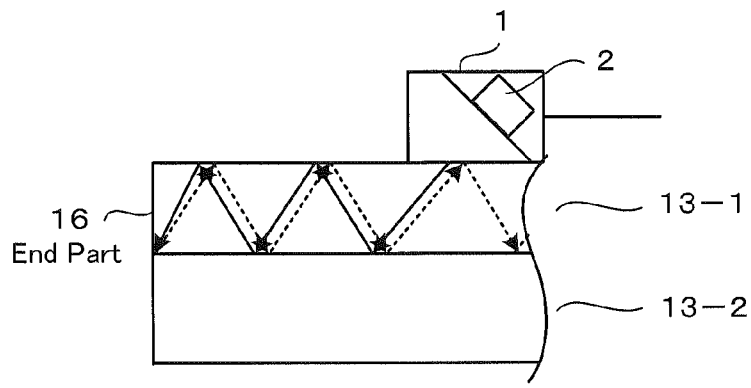
FIG. 15 is a drawing for explaining a concrete example of the welding inspection method using an ultrasonic wave according to the embodiment of the present invention (in the case where the nugget is not made up normally, having a pealed between the steel plates)
Figure 16:
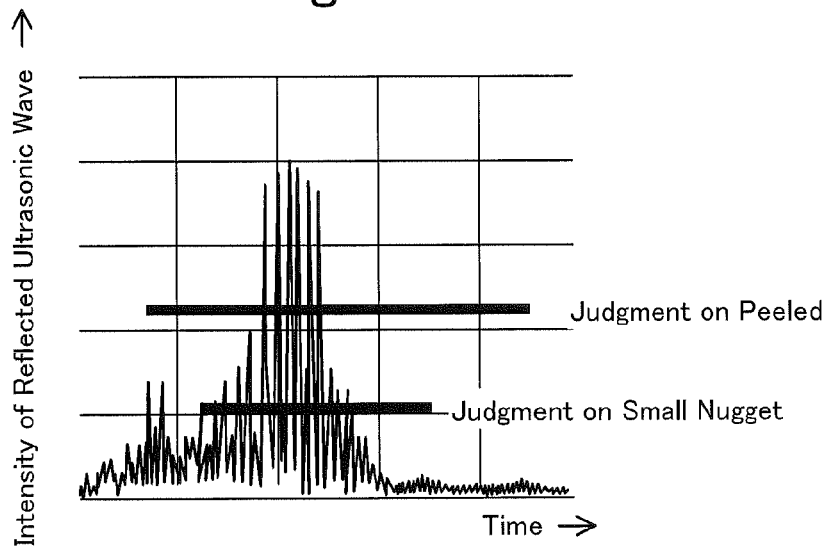
FIG. 16 shows a graph of an inspection result of the welding inspection method according to the embodiment of the present invention on the defective nugget having the pealed between the steel plates.

FIG. 15 is a drawing for explaining a case where the nugget 12 is not made up normally, having a pealed between the steel plates 13-1 and 13-2. FIG. 16 shows a graph of an inspection result on the nugget 12 being defective with the pealed between the steel plates 13-1 and 13-2; and in the graph, a horizontal axis and a vertical axis are a time axis and axis of an intensity of the reflected ultrasonic wave, respectively.

As shown in FIG. 15, if the nugget 12 has a pealed between the steel plates 13-1 and 13-2, the ultrasonic wave having entered the steel plate 13-1 from the probe 1 does not enter the steel plate 13-2 and gets reflected at an end part of the steel plate 13-1. Since the reflected ultrasonic wave is further reflected repeatedly within steel plate 13-1, there appears a reflected ultrasonic wave having a high intensity, as shown in FIG. 16.

Figure 17:
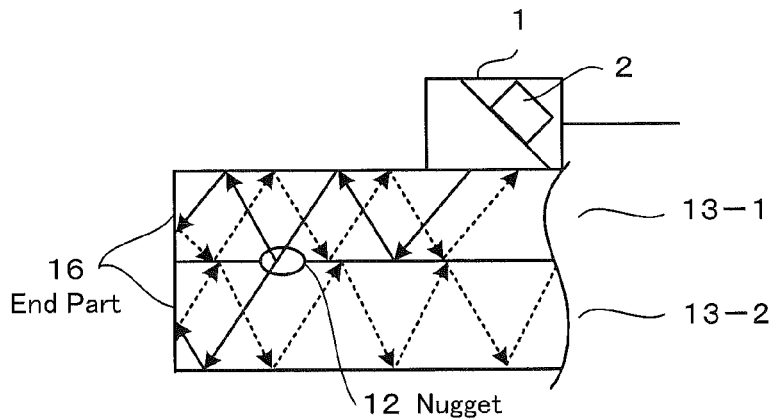
FIG. 17 is a drawing for explaining a concrete example of the welding inspection method using an ultrasonic wave according to the embodiment of the present invention (in the case where the nugget is made to be small)
Figure 18:
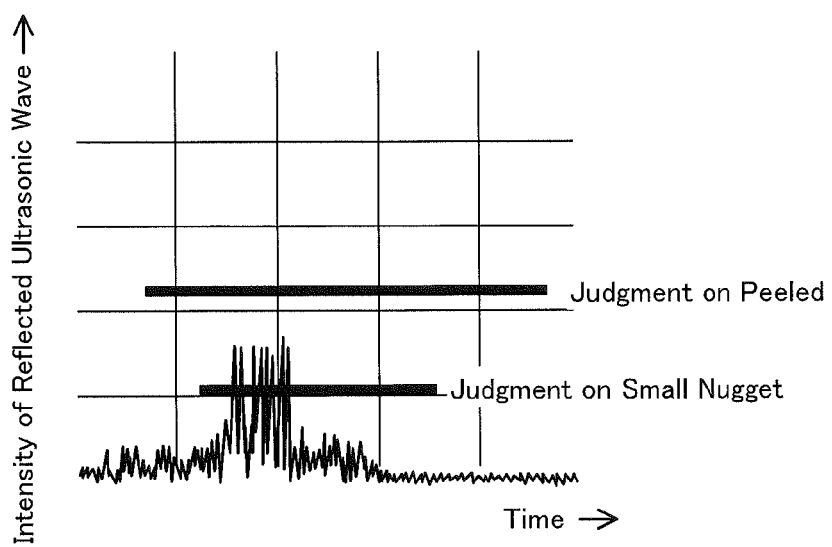
FIG. 18 shows a graph of an inspection result of the welding inspection method according to the embodiment of the present invention on the small nugget.

FIG. 17 is a drawing for explaining a case where the nugget 12 is made to be small. FIG. 18 shows a graph of an inspection result on the nugget 12 being made to be small; and in the graph, a horizontal axis and a vertical axis are a time axis and axis of an intensity of the reflected ultrasonic wave, respectively.

As shown in FIG. 17, if the nugget 12 is made to be small, a part of the ultrasonic wave having entered the steel plate 13-1 from the probe 1 passes through the small nugget 12 to enter the steel plate 13-2. However, the remainder of the ultrasonic wave is reflected at the end part of the steel plate 13-1. Then, the reflected ultrasonic wave is further reflected repeatedly within steel plate 13-1. Accordingly, as shown in FIG. 18, there appears a reflected ultrasonic wave having a higher intensity than the nugget 12 normally made up shows as indicated in FIG. 14.

Thus, a judgment can be made for each case of the nugget 12 being made up normally, the nugget 12 being defective with the pealed between the steel plates 13-1 and 13-2, and the nugget 12 made to be smaller than specified according to standards.

In a display mode of the display part 7, waveform images themselves of the reflected ultrasonic waves may be displayed as shown in FIG. 14, FIG. 16, and FIG. 18 to allow the inspector to visually check for recognition and make a judgment. Otherwise, according to an intensity of the reflected ultrasonic wave analyzed by the data analyzer 5, the display control part 6 may display textual information indicating "Normal", "Pealed Exist", "Small Nugget", etc. Alternatively, the information of indicating "Normal", "Pealed Exist", "Small Nugget", etc. may be output to the external device 9. It is also possible to have the display part 7 display a waveform and/or information, and at the same time to output the information to the external device 9. As outputting information to the external device 9, possible are various operation modes such as; logging inspection data automatically, sending inspection results to multiple destinations, and warning of an abnormal inspection result.

Figure 19:
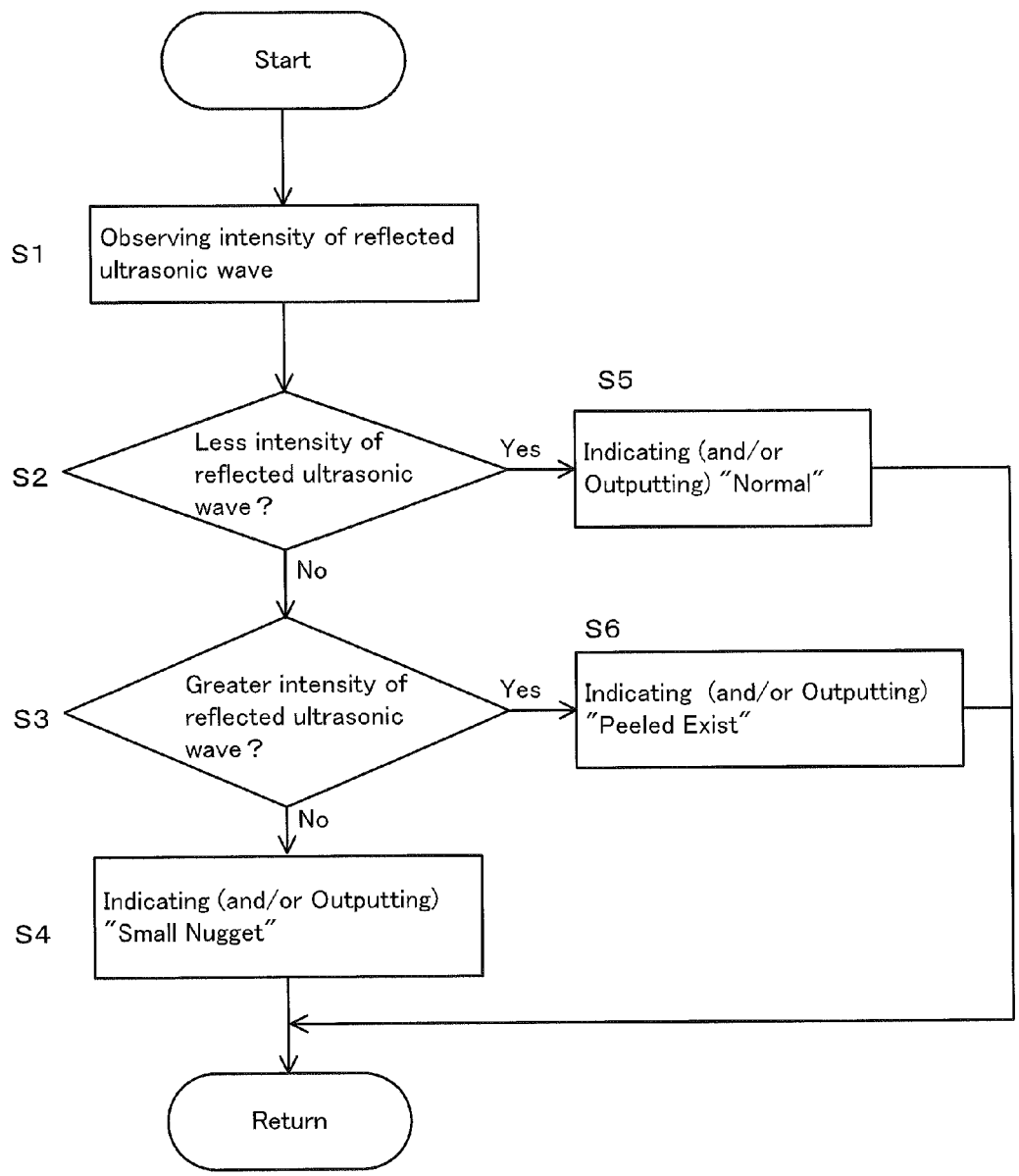
FIG. 19 is a flowchart showing processing procedures by a display control part according to the embodiment of the present invention.

FIG. 19 is a flowchart showing processing procedures by the display control part 6 in the latter of the two cases described above. More specifically, as shown in FIG. 19, the display control part 6 observes the intensity of the reflected ultrasonic wave analyzed by the data analyzer 5 (Step S1); and if the intensity of the reflected ultrasonic wave is less than a prescribed value ("Yes" of Step S2), the display part 7 indicates "Normal" and/or the information of "Normal" is output to the external device 9 (Step S5). If the intensity of the reflected ultrasonic wave is neither less than the prescribed value ("No" of Step S2) nor greater than a prescribed value ("No" of Step S3), the display part 7 indicates "Small Nugget" and/or the information of "Small Nugget" is output to the external device 9 (Step S4). Otherwise, if the intensity of the reflected ultrasonic wave is greater than the prescribed value ("Yes" of Step S3), the display part 7 indicates "Pealed Exist" and/or the information of "Pealed Exist" is output to the external device 9 (Step S6).

(Practical Example of Supportive Device for Inspection)

Figure 20:
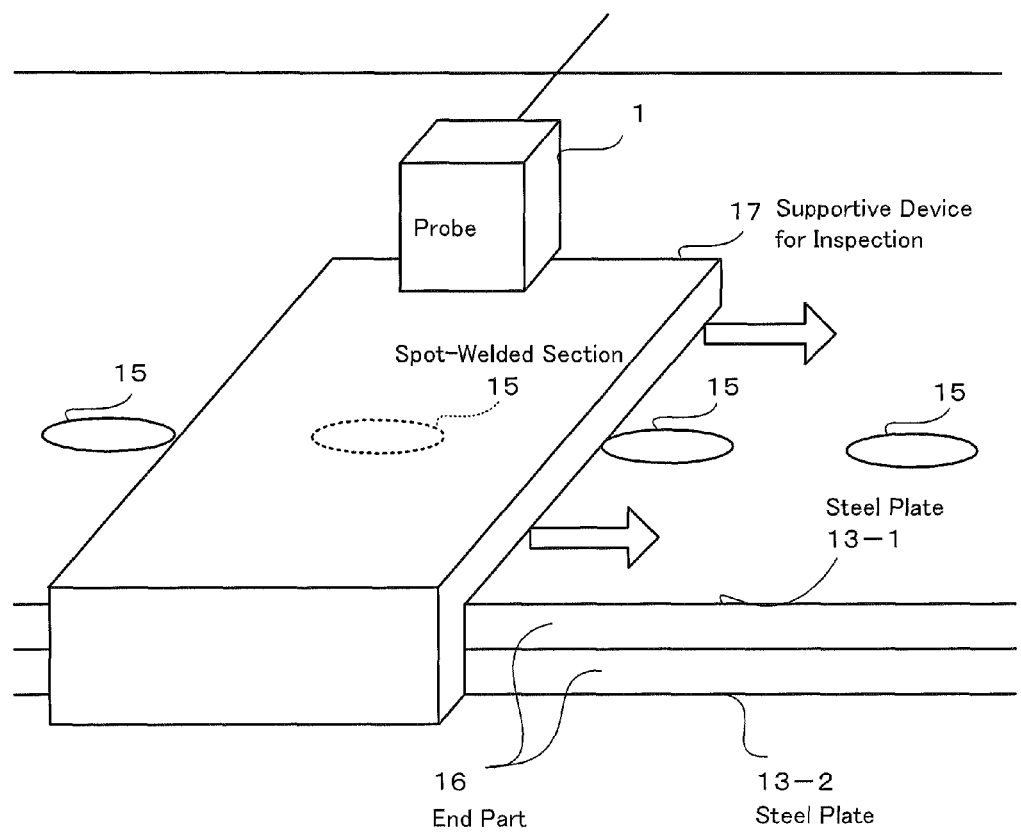
FIG. 20 is a drawing for explaining a supportive device for inspection (a perspective view)
Figure 21:
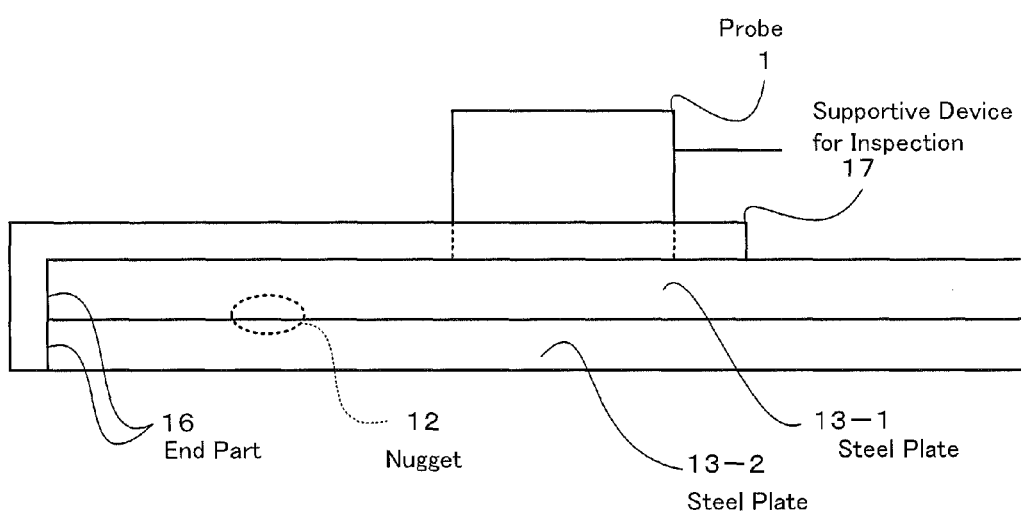
FIG. 21 is a drawing for explaining the supportive device for inspection (a side view)

A practical example of a supportive device for inspection is explained below with reference to FIGS. 20 and 21, which are drawings for explaining the supportive device for inspection 17. FIGS. 20 and 21 are a perspective view and a side view of the supportive device, respectively. It is often the case that spot-welded sections are placed in series on the steel plate 13-1 as shown in FIG. 20. In this case, a distance between the end part 16 and spot-welded sections 15 provided in plural is almost constant. Therefore, if once a distance from the end part 16 to the probe 1 is determined, sliding the probe 1 in a longitudinal direction of the steel plates 13-1 and 13-2 enables successive inspection of the spot-welded sections 15 provided in plural.

More specifically, as shown in FIGS. 20 and 21, while a top section of the supportive device for inspection 17 being bent at a right angle, the top section is attached onto the end part 16. Then, the distance from the end part 16 to the probe 1 can be kept constant. Accordingly, inspection can be carried out successively for the spot-welded sections 15 provided in series and in plural on the steel plate 13-1.

Though it is not shown in the drawing, the supportive device for inspection 17 includes a mechanism with which a position of the probe 1 can be adjusted on the supportive device for inspection 17. Then, while the top section of the supportive device for inspection 17 being bent at a right angle, the top section is attached onto the end part 16 to adjust an appropriate position of the probe 1 in relation to one of the spot-welded sections 15. After adjusting the appropriate position of the probe 1, sliding the supportive device for inspection on the steel plates 13-1 and 13-2 makes it possible to have appropriate positions of the probe 1 for the others of the spot-welded sections 15 as well. Thus, using the supportive device for inspection 17 can greatly improve the inspection work efficiency.

(Explanation about Advantageous Effects)

By using the welding inspection method according to the embodiment of the present invention, the problems that the conventional method has can be solved as described above. Furthermore, there exists another effect that inspection can be carried out, being independent from a form accuracy of a welded part. The effect is explained below with reference to FIGS. 22A to 22C, 23 and 24.

Figure 22A:
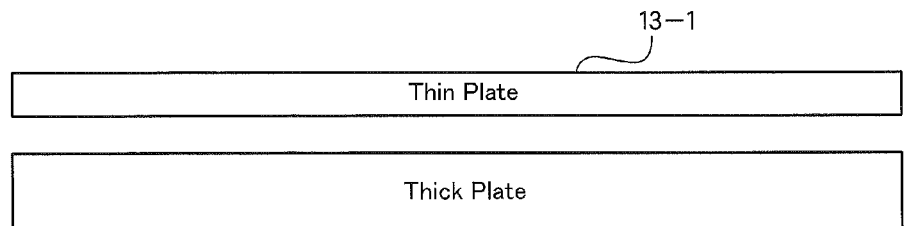
FIGS. 22A to 22C are drawings for explaining an example of deterioration of a form accuracy of a welded part.
Figure 22B:
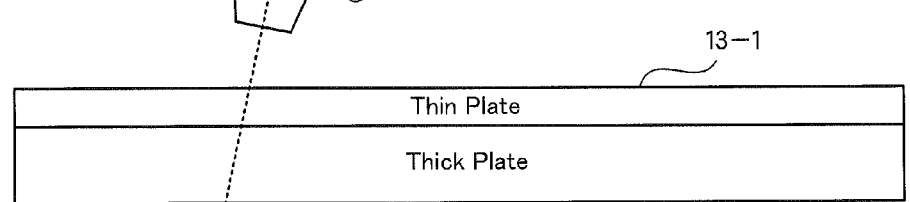
Figure 22C:
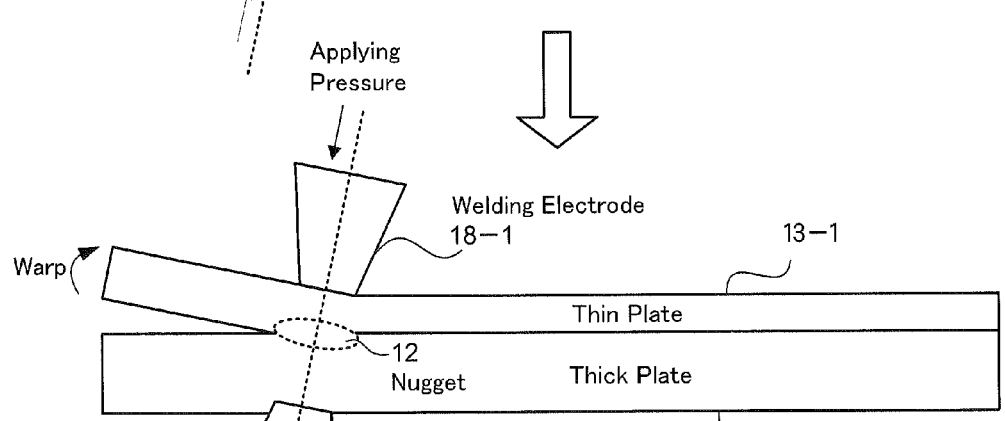

An example of deterioration of a form accuracy of a welded part is explained with reference to FIGS. 22A to 22C. FIGS. 22A-22C are drawings for explaining an example of deterioration of a form accuracy of a welded part. For example, the steel pate 13-1 is a thin plate while the steel plate 13-2 is a thick plate as shown in FIG. 22A. Under such a condition, if welding electrodes 18-1 and 18-2 contact the steel plates 13-1 and 13-2 in a little tilted direction as shown in FIG. 22B, the thin steel plate 13-1 may have a warp after the welding due to a stress generated by applying pressure with the welding electrodes 18-1 and 18-2 as shown in FIG. 22C. In this way, a welded part where exists the nugget 12 may not be regularly shaped.

Figure 23:
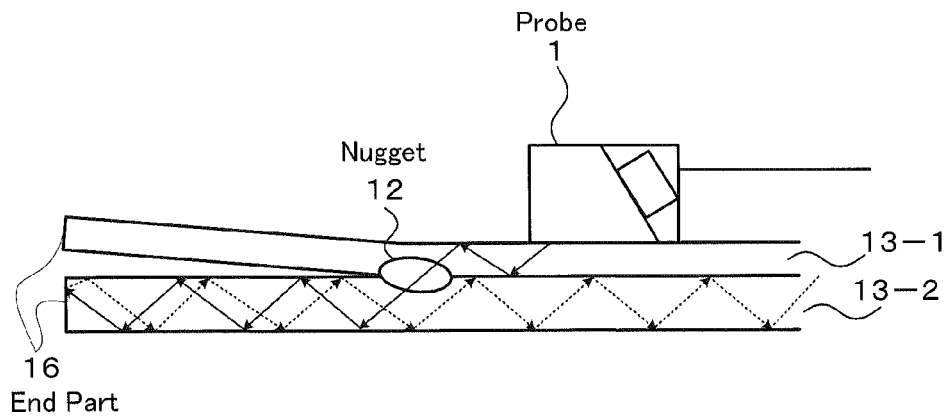
FIG. 23 is a drawing of inspection by the welding inspection method according to the embodiment of the present invention at a welded part that is not regularly shaped.
Figure 24:
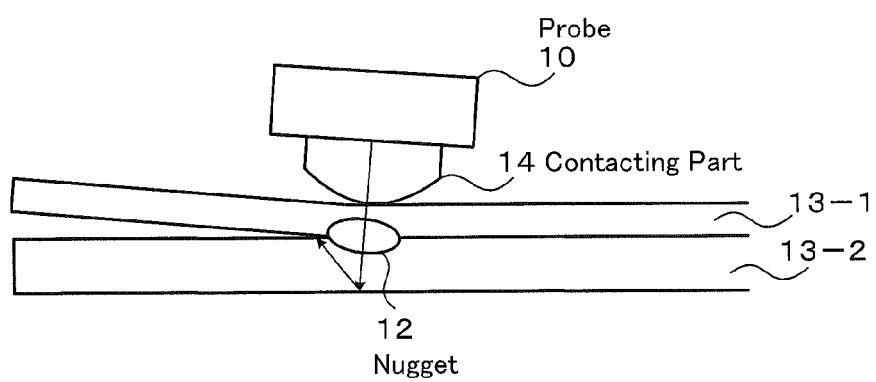
FIG. 24 is a drawing of inspection by a conventional welding inspection method at the welded part that is not regularly shaped.

FIG. 23 is a drawing of inspection by the welding inspection method according to the embodiment of the present invention at a welded part that is not regularly shaped. Meanwhile, FIG. 24 is a drawing of inspection by a conventional welding inspection method at the welded part that is not regularly shaped. As shown in FIG. 23, in the welding inspection method according to the embodiment of the present invention, the ultrasonic wave having entered the steel plate 13-1 passes through the nugget 12 to enter the steel plate 13-2, and then the ultrasonic wave is reflected at the end part 16. Accordingly, the inspection can be carried out without any problem.

Contrarily, as shown in FIG. 24, it is indispensable in the conventional welding inspection method to receive the reflected ultrasonic wave coming from the bottom surface of the steel plate 13-2. Therefore, when a reflecting surface for the ultrasonic wave is not perpendicular to an incident direction of the ultrasonic wave, the ultrasonic wave is reflected in a direction that is not oriented toward the probe 10. As a result, it is hardly possible to carry out inspection accurately.

Thus, in the welding inspection method according to the embodiment of the present invention, inspected can be even the steel plates 13-1 and 13-2 including a welded part that is not regularly shaped.

Figure 25:
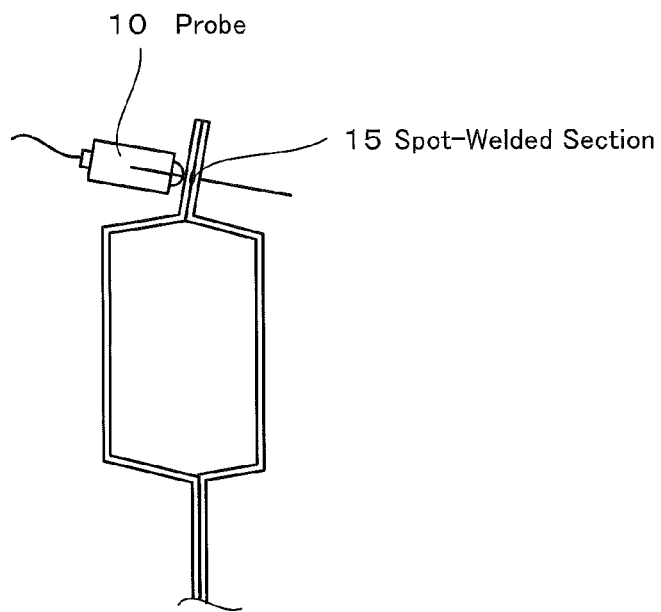
FIG. 25 is a drawing of inspection at a single position for a spot-welded section by using a conventional welding inspection method.

FIG. 25 is a drawing of inspection at a single position for the spot-welded sections 15 by using the conventional welding inspection method. As shown in FIG. 25, it is necessary in the conventional welding inspection method to place the probe 10 to be perpendicular to the steel plate having the spot-welded sections 15, and therefore it is impossible to carry out inspection at a plurality of positions for the single spot-welded sections 15.

Figure 26:
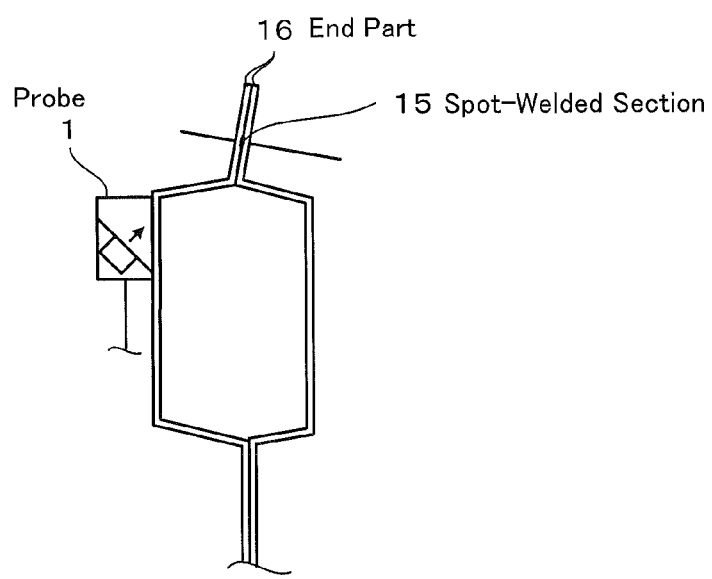
FIG. 26 is a drawing of inspection at a plurality of positions for a spot-welded section.
Figure 27:
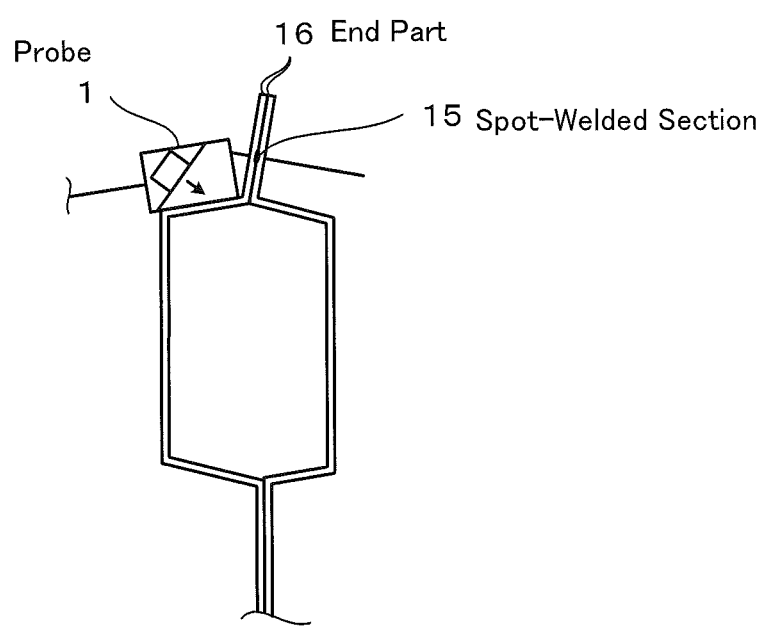
FIG. 27 is a drawing of inspection at a plurality of positions for a spot-welded section.

However, in the welding inspection method according to the embodiment of the present invention, inspection can be carried out at a plurality of positions for the single spot-welded sections 15. FIGS. 26 and 27 are drawings of inspection at a plurality of positions for the single spot-welded section 15. Thus, in the welding inspection method according to the embodiment of the present invention, inspection can be carried out at a position shown in FIG. 26 as well as another position shown in FIG. 27 for the single spot-welded sections 15. More specifically, inspection can be carried out as far as the conditions are met; i.e., the spot-welded section 15 exists between the probe 1 and the end part 16, and the ultrasonic wave launched from the probe 1 is reflected at the end part 16. For example, even in the case of a bent steel plate, inspection for a welded part located behind the bent point can be carried out at a position before the bent point, as far as the bent part does not interfere with the travel of the ultrasonic wave.

Furthermore, as described above, a welded part that is not regularly shaped can still be inspected, and therefore restrictions on setting of inspecting positions can be eased. Thus, being compared with the conventional welding inspection method, the welding inspection method according to the embodiment of the present invention can improve the inspection accuracy.

INDUSTRIAL APPLICABILITY

According to the present invention, welding inspection can be carried out accurately, being irrelevant to the skill level of the inspector. Furthermore, the probe is not worn out and/or damaged easily. Moreover, the inspection result does not depend on the accuracy of the form of the welded section. As a result, the present invention can be applied for development of a welding inspection apparatus for automatic inspection in a production line.

The invention claimed is:

1. A welding inspection method, comprising:
launching an ultrasonic wave from a probe to a welded part where a welding has been carried out for a plurality of stacked metal plates;
receiving a reflected wave of the ultrasonic wave reflected inside the stacked metal plates and at the welded part, by means of the probe at the same location as the ultrasonic wave being launched, to check quality of the welding;
wherein the ultrasonic wave is launched to a boundary plane of the stacked metal plates by the probe being temporarily placed in the proximity of the welded part on a surface of the stacked metal plates, such that a propagation direction of the ultrasonic wave is oblique to a surface of the stacked metal plates when the ultrasonic wave enters the metal plates; and
analyzing how the ultrasonic wave passing through the stacked metal plates, reflected at an end of the stacked metal plates and returned to the probe is affected by the welded part.

2. The welding inspection method according to claim 1:
wherein the probe is temporarily placed at such a position that an ultrasonic wave having entered the boundary plane from an oblique direction passes through the welded part created in the boundary plane of the plurality of metal plates.

3. The welding inspection method according to claim 1:
wherein display processing means displays an image of a reflected wave of the ultrasonic wave.

4. The welding inspection method according to claim 1:
wherein display processing means displays the contents of an inspection result estimated according to an intensity of the reflected wave of the ultrasonic wave.

5. The welding inspection method according to claim 1:
wherein display processing means outputs information showing the inspection result estimated according to the intensity of the reflected wave of the ultrasonic wave, to an external device.

6. The welding inspection method according to claim 1:
wherein the welding is carried out as a spot welding.

7. A welding inspection apparatus for quality check on a welding carried out for a plurality of stacked metal plates, comprising:
a probe for transmitting and receiving an ultrasonic wave;
means for launching an ultrasonic wave from the probe to a welded part where a welding has been carried out for a plurality of stacked metal plates;
means for receiving a reflected wave of the ultrasonic wave reflected inside the stacked metal plates and at the welded part, by means of the probe at the same location as the ultrasonic wave being launched, to check quality of the welding; and
means for analyzing how the ultrasonic wave passing through the staked metal plates, reflected at an end of the stacked metal plates and returned to the probe is affected by the welded part when the probe is temporarily placed on a surface of the stacked metal plates at the proximity of the welded part and the ultrasonic wave is launched to a boundary plane of the stacked metal plates with a propagation direction of the ultrasonic wave being oblique to the surface of the stacked metal plates at the ultrasonic wave entering the metal plates.

8. The welding inspection apparatus according to claim 7:
further comprising display processing means for displaying an image of a reflected wave of the ultrasonic wave.

9. The welding inspection apparatus according to claim 7:
further comprising display processing means for displaying the contents of an inspection result estimated according to an intensity of the reflected wave of the ultrasonic wave.

10. The welding inspection apparatus according to claim 7:
further comprising display processing means for outputting information showing the inspection result estimated according to the intensity of the reflected wave of the ultrasonic wave, to an external device.

* * * * *